United States Patent
Osypka

(10) Patent No.: US 8,160,723 B2
(45) Date of Patent: Apr. 17, 2012

(54) BIPOLAR ELECTRODE THAT CAN BE IMPLANTED

(76) Inventor: Peter Osypka, Rheinfelden-Herten (DE)

(*) Notice: Subject to any disclaimer, the term of this patent is extended or adjusted under 35 U.S.C. 154(b) by 524 days.

(21) Appl. No.: 12/356,784

(22) Filed: Jan. 21, 2009

(65) Prior Publication Data
US 2009/0221895 A1 Sep. 3, 2009

(30) Foreign Application Priority Data
Jan. 22, 2008 (DE) .......... 10 2008 005 378

(51) Int. Cl.
*A61N 1/05* (2006.01)
(52) U.S. Cl. .......... 607/127
(58) Field of Classification Search .......... None
See application file for complete search history.

(56) References Cited

U.S. PATENT DOCUMENTS

| | | | |
|---|---|---|---|
| 4,570,642 A * | 2/1986 | Kane et al. | 607/127 |
| 4,649,938 A * | 3/1987 | McArthur | 607/127 |
| 5,324,325 A | 6/1994 | Moaddeb | |
| 5,716,390 A | 2/1998 | Li | |
| 6,813,521 B2 * | 11/2004 | Bischoff et al. | 607/122 |
| 7,305,270 B1 * | 12/2007 | Kroll et al. | 607/127 |
| 7,383,091 B1 * | 6/2008 | Chitre et al. | 607/127 |
| 7,840,283 B1 * | 11/2010 | Bush et al. | 607/127 |
| 2002/0188338 A1 | 12/2002 | Bischoff | |
| 2006/0036306 A1 | 2/2006 | Heist et al. | |
| 2006/0064159 A1 | 3/2006 | Porter et al. | |

FOREIGN PATENT DOCUMENTS

| WO | WO 95/20360 | * | 8/1995 |
|---|---|---|---|
| WO | 2007073435 | | 6/2007 |
| WO | 2008066423 | | 6/2008 |

* cited by examiner

*Primary Examiner* — Kennedy Schaetzle
(74) *Attorney, Agent, or Firm* — Volpe and Koenig, P.C.

(57) ABSTRACT

A bipolar electrode (1) that can be implanted is provided with at least two poles at its distal end, namely a cathode (4) and an anode (6) spaced apart therefrom. Further, an anchoring is provided at the distal end of the electrode (1), provided for example as a helical screw (5). The different poles are arranged on different shafts or tubes (3) and (7) displaceable in reference to each other, in which the exterior shaft or tube (7) first can be pushed over the anchor (5) in order to protect it during implantation. In the operational state, the poles are adjusted by a relative motion of the two shafts carrying them with regard to their relative positioning.

6 Claims, 1 Drawing Sheet

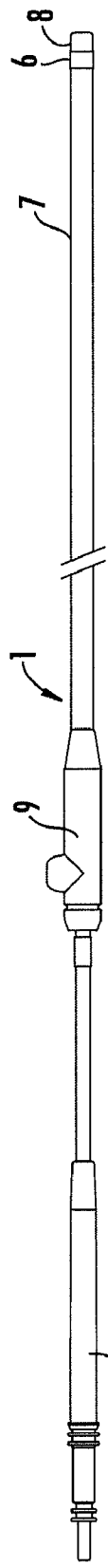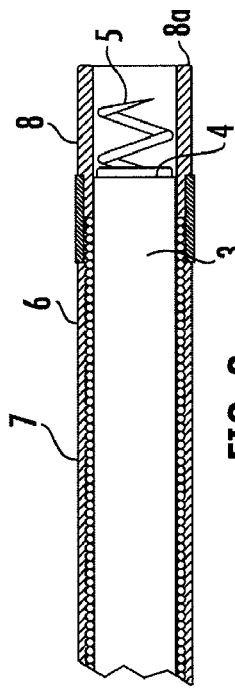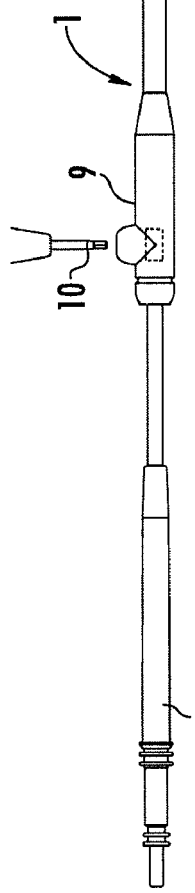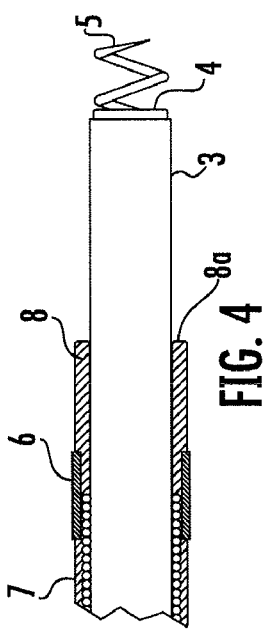

BIPOLAR ELECTRODE THAT CAN BE IMPLANTED

CROSS-REFERENCE TO RELATED APPLICATIONS

This application claims the benefit of DE 10 2008 0005 378.3, filed Jan. 22, 2008, which is incorporated by reference herein as if fully set forth.

BACKGROUND

The invention relates to a bipolar electrode that can be implanted having a cathode, located at its distal end and carried by a shaft or a tube, and an anode spaced apart therefrom, with the electrode having an anchor at the distal end for fastening in the tissue of a heart, with the bipolar electrode being formed from two unipolar electrodes, one of which is provided with the cathode or the anchor or anchors at its distal end and the other one of which is provided with the anode at a second shaft or tube, with the second shaft accepting the first shaft provided with the cathode and being adjustable or displaceable in reference thereto in the axial direction and with the cathode and the anode each being electrically connected to a bipolar plug at least in the operational position.

Such a bipolar electrode is known from U.S. 2006/064159 A 1. Here, prongs or bendable pins are provided as anchors at the anode connected to the second shaft, located at the exterior, which can only become effective when the head of said shaft can be inserted sufficiently deep into the tissue. Such barbed pins can cause collisions or interlocking, primarily when passing through the nitral cap. If the anchor at the distal end of the cathode was embodied as a helical electrode or helical screw, the wall of the tissue or tissues through which the electrodes must be pushed towards the heart could be injured.

Pacemaker electrodes with helical screws serving for anchoring are known, for example from U.S. Pat. No. 5,716, 390, which during implantation are retracted in the tube of the electrode and can be axially displaced in the heart with the aid of a special mechanism for the anchoring process to be performed, however this requires considerable expenses. Possible interlocking with pin-shaped or barb-like anchors has been tolerated in the past.

SUMMARY

Therefore the object of the invention is to provide an electrode of the type mentioned at the outset, by which a smooth implantation in the heart is possible, without risking injuries by the helical electrode or interlocking by the pin-shaped anchors.

In order to attain this object, it is provided that during implantation the second shaft accepts the anchor, embodied as a helical screw, in its body and encases it and that the second shaft, provided with the anode, is axially adjustable in reference to the first shaft to the extent of the helical screw in reference to the distal end of the first shaft.

Therefore, in the operational position, both poles, i.e. the cathode and the anode, which in turn may be provided in several versions each, are connected to a bipolar plug to be connected to a pacemaker, so that the entire arrangement represents a bipolar electrode. During the implantation it is also possible to have the shaft or tube carrying the anode being provided displaced to such an extent that the anchoring located at the shaft or tube provided with the cathode is encased thereby so that during the implantation no injuries can occur by a helical anchoring nor any interlocking of pin-shaped anchors. When the electrode has reached its target with its distal end, the shaft carrying the anode can be retracted into its normal operational position and the anchoring can be performed inside the heart, with expensive mechanisms for the axial adjustment of a helical anchoring not being necessary, but being avoided.

Due to the fact that the second shaft provided with the anode is axially adjustable or retractable in reference to the first shaft by the length of the anchor embodied as a helical screw projects in reference to the distal end of the first shaft, the lengths of this helical screw serving as an anchor cannot be used in its entirety during said anchoring. The helical screw may also be encased entirely by the second tube or shaft during the implantation so that injuries of the tissue are avoided.

A beneficial embodiment of the invention may provide that the second shaft carrying the anode concentrically encases the first shaft provided with the cathode. The shafts may therefore show an approximately circular cross-section, which if necessary also allows or facilitates a rotation of the entire electrode or a relative rotation of the two shafts in reference to each other.

Another advantageous embodiment of the invention may comprise that the second shaft carrying the anode is provided at its distal end, adjacent to the anode, with a sheath-like insulating piece, preferably an extension of the tubular shaft in reference to the anode, which projects in reference to the anode. This way it is possible in the operational state to retract the shaft or tube carrying the anode only to such an extent that the anchor located at the first shaft can be inserted into the cardiac tissue, but that the insulating piece contacts the cardiac wall at the inside in order to ensure an optimal impulse conduction between the poles, i.e. between the anode and the cathode, through the cardiac tissue and thus to keep any loss as small as possible in this area.

The relative mobility of the two poles due to the relative ability to displace the two shafts or tubes carrying these poles therefore allows, on the one hand, the protection of the anchor located at the cathode during the implantation and, on the other hand, a best possible arrangement for the flux of the impulse current in the operational position.

The second shaft or tube carrying the anode can be provided with a coupling at its proximal end, which can be displaced or fixed or fastened in reference to the first shaft located inside. This fixation can here already exist during the process of implantation, then be released for the relative displacement of the two shafts in reference to each other, and again be set in the displaced position. Here, the second shaft can be fixable in the area of the coupling via a clamping screw that can be released, which represents a particularly simple type of fixation.

Further, it is possible that at least one clamping screw simultaneously contacts the electric connection between the anode and the bipolar plug or a wire section leading thereto. This facilitates the entire design of the electrode.

Another possible embodiment of the invention may comprise that the cathode and the anode can be arranged at an optional distance in reference to each other by the ability relative for displacement of the shafts or tubes carrying them. It is also possible for the two poles to be spatially adjustable or movable in reference to each other, in order to either allow it to be adjusted to the different anatomies in the area of the interior cardiac wall or to allow creating an optimal mutual distance after the anchoring of the cathode.

Primarily combinations of one or several of the above-described features and measures result in a bipolar electrode that can be implanted, in which the anchoring, preferably a helical screw, is arranged unchangeable in a fixed manner at the shaft or tube carrying the cathode, but still can be covered during the implantation, because for the second pole, namely the anode, another shaft or tube is provided, which is sufficiently displaceable in reference to the first shaft or tube to accept in its body the anchoring at the cathode during the implantation. The shaft or tube carrying the anode therefore has a dual function, because during the implantation it can form a protection against injury or interlocking in the area of the anchoring.

BRIEF DESCRIPTION OF THE DRAWINGS

In the following, an exemplary embodiment of the invention is described in greater detail using the drawing. Shown in partially schematic illustration are:

FIG. 1 is a side view of a bipolar electrode according to the invention that can be implanted, with a second shaft or tube carrying the anode being displaced towards the distal end in reference to the first shaft carrying the cathode, FIG. 2 is a longitudinal cross-section through the end of the electrode according to FIG. 1, with the projected shaft carrying the anode encasing and completely accepting an anchoring serving as a helical screw located at the end of the first shaft providing the cathode, FIG. 3 is a view according to FIG. 1 after the retraction of the shaft carrying the anode in reference to the shaft provided with the cathode and the anchoring, and FIG. 4 is a view according to FIG. 2 after the shaft carrying the anode has been retracted, with the helical screw serving as an anchor being released or exposed.

DETAILED DESCRIPTION OF THE PREFERRED EMBODIMENTS

A bipolar electrode that can be implanted, in its entirety marked 1, is provided at its proximal end with a bipolar plug 2, by which the electrode 1 can be connected to a pacemaker.

A cathode 4 carried by a first shaft or tube 3 is located at its distal end, with the cathode 4 here also may be embodied as a helical screw 5 serving as an anchor. The electrode 1 is therefore provided at the distal end with an anchor 5 for fastening in the tissue of the heart. Further, an anode 6 is provided, at least in the operational position spaced apart from the cathode 4, so that therefore two poles 4 and 6 make the electrode 1 bipolar.

When comparing all figures it becomes clear that this bipolar electrode 1 actually is formed by two unipolar electrodes, with one of them being provided with the cathode 4 and the anchor 5 at its distal end and with its other one being provided or carrying the anode 6 at a second shaft or tube 7. Here, it is also possible to provide two cathodes 4 and/or anodes 6.

Furthermore, by comparing FIG. 1 to FIG. 3 and FIG. 2 to FIG. 4 it is discernible that the second shaft 7 accepts and/or concentrically encapsulates the first shaft or tube 3 carrying the cathode 4 and that these two shafts 3 and 7 are adjustable or displaceable in the axial direction in reference to each other. At least in the operational position shown in FIGS. 3 and 4, here the cathode 4 and the anode are each electrically connected to the bipolar plug 2.

It is also possible to implant the electrode 1 in the displaced position of the two shafts 3 and 7 shown in FIG. 1 without risking that the helical screw 5 serving as the anchor leads to injuries of the blood vessels through which the implantation occurs. Additionally, interlocking is avoided at the entry into the heart itself by the second shaft 7 accepting the helix 5 in this position.

The second shaft or tube 7 carrying the anode 6, concentrically encasing the first shaft 3, is here axially adjustable in reference to the first shaft 3 by an amount considerably exceeding the axial extension of the anchoring or the helical screw 5 serving for the anchoring so that in the operational position according to FIGS. 3 and 4, on the one hand, the desired distance is set between the anode and the cathode, and on the other hand, a good anchoring is also ensured.

Here, it is discernible in FIGS. 2 and 4 that the second shaft or tube 7 carrying the anode 6 is provided at its distal end with a sheath-like insulating piece 8, adjacent to the anode 6, which projects in reference to the anode 6 and can form an extension of the tubular shaft 7. It is also possible after the implantation and anchoring to displace the second shaft 7 again to such an extent that the facial end 8a of this insulating piece rests at the inside of the cardiac wall contacting it in order to achieve optimal conduction of the stimulating current between the two poles and thus to keep loss as small as possible in this area.

The second shaft or tube 7 carrying the anode 6 is provided at its proximal end with a coupling marked 9 in its entirety, which is displaceable or fixable or settable in reference to the first shaft 3 located inside. Here, in the area of the coupling 9 the second shaft 7 can be fixed via a clamping screw that can be released, with its operation being indicated by a respective tool 10 in FIG. 3. In a released clamping screw, the relative displacement of the two shafts can be performed, which can then be fixed both during the implantation as well as in the later operational position.

Here, this clamping screw can simultaneously create or contact the electric connection between the anode and the bipolar plug 2 or a wire section leading thereto so that in the operational position the poles of the overall bipolar electrode 1 are connected to the bipolar plug 2.

The bipolar electrode 1 that can be implanted is provided at its distal end with at least two poles, namely a cathode 4 and an anode 6 spaced apart therefrom. Further, an anchoring is provided at the distal end of the electrode 1, provided for example as a helical screw 5. The different poles are arranged on different shafts or tubes 3 and 7, displaceable in reference to each other, with the exterior shaft or tube 7 first being pushed over and beyond the anchor 5 in order to protect it during the implantation, in the operational position the poles are then adjusted by a relative motion of the two shafts carrying them with regard to their mutual distance.

The invention claimed is:

1. A bipolar electrode (1) that can be implanted, comprising two unipolar electrodes, with one including a cathode (4) located at a distal end of a first shaft or tube (3), and the other comprising an anode (6) spaced apart therefrom and located on a second shaft or tube, with the second shaft or tube (7) encasing the first shaft or tube (3) provided with the cathode (4) and being displaceable or shiftable in reference thereto in an axial direction, the cathode, which includes an electrode provided with at least one anchor (5) at the distal end adapted for fastening in the tissue of the heart at least in an operational position of the cathode (4), and the anode (6) each are electrically connected to a bipolar plug (2), the second shaft (7) accepts and encases the anchor (5), which comprises a helical screw (5), during the implantation and the second shaft (7) provided with the anode (6) is axially adjustable in reference to the first shaft (3) at least by a length of the helical screw (5) in reference to the distal end of the first shaft (3), and the second shaft (7) carrying the anode (6) is provided with a coupling (9) at its proximal end, which is displaceable and fixable or settable in reference to the first shaft (3) located therein.

2. An electrode according to claim 1, wherein the second shaft carrying the anode concentrically encases the first shaft provided with the cathode.

3. An electrode according to claim 1, wherein the second shaft (7) carrying the anode (6) is provided at a distal end thereof adjacent to the anode (6) with a sheath-like insulating piece (8) which projects in reference to the anode.

4. An electrode according to claim 3, wherein the sheath-like insulating piece (8) is an extension of the tubular shaft (7) in reference to the anode.

5. An electrode according to claim 1, wherein the second shaft (7) can be fixed in an area of the coupling (9) via a clamping screw that can be released.

6. A bipolar electrode (1) that can be implanted, comprising two unipolar electrodes, with one including a cathode (4) located at a distal end of a first shaft or tube (3), and the other comprising an anode (6) spaced apart therefrom and located on a second shaft or tube, with the second shaft or tube (7) encasing the first shaft or tube (3) provided with the cathode (4) and being displaceable or shiftable in reference thereto in an axial direction, the cathode, which includes an electrode provided with at least one anchor (5) at the distal end adapted for fastening in the tissue of the heart at least in an operational position of the cathode (4), and the anode (6) each are electrically connected to a bipolar plug (2), the second shaft (7) accepts and encases the anchor (5), which comprises a helical screw (5), during the implantation and the second shaft (7) provided with the anode (6) is axially adjustable in reference to the first shaft (3) at least by a length of the helical screw (5) in reference to the distal end of the first shaft (3), and at least one clamping screw simultaneously contacts an electrical connection between the anode and the bipolar plug (2) or a wire section leading thereto.

* * * * *